United States Patent [19]

Metianu et al.

[11] Patent Number: 4,479,935

[45] Date of Patent: Oct. 30, 1984

[54] FRACTIONS EXTRACTED FROM AEROBIC BACTERIA, ENDOWED WITH ANTITUMORAL, ANTIBACTERIAL AND INTERFERON INDUCING PROPERTIES, AND PROCESS FOR THEIR PREPARATION

[75] Inventors: Tiberius Metianu, Charenton; Bernard Bizzini, Paris, both of France

[73] Assignee: Institut Pasteur, Paris, France

[21] Appl. No.: 254,254

[22] Filed: Apr. 15, 1981

[30] Foreign Application Priority Data

Apr. 22, 1980 [FR] France ............................. 80 08976
Mar. 30, 1981 [FR] France ............................. 81 06294

[51] Int. Cl.$^3$ .......................... A61K 39/05; C12N 1/20
[52] U.S. Cl. ...................................... 424/92; 424/88; 424/93; 435/253
[58] Field of Search .............................. 424/85–92, 424/93; 435/253

[56] References Cited

U.S. PATENT DOCUMENTS

| | | | |
|---|---|---|---|
| 3,679,654 | 7/1972 | Maes | 424/85 |
| 3,852,420 | 12/1974 | Usdin | 424/92 |
| 3,852,423 | 12/1974 | Nakase | 424/85 |
| 3,928,565 | 12/1975 | Homa et al. | 424/92 |
| 4,001,395 | 1/1977 | Jolles et al. | 424/92 |
| 4,007,086 | 2/1977 | Hamilton | 424/85 |
| 4,010,257 | 3/1977 | Adlam et al. | 424/92 |
| 4,013,788 | 3/1977 | Jolles et al. | 424/92 |
| 4,042,678 | 8/1977 | Ciobaru et al. | 424/92 |
| 4,076,801 | 2/1978 | Fauve | 424/92 |
| 4,079,126 | 3/1978 | Hommo et al. | 424/92 |
| 4,180,563 | 12/1979 | Fauve | 424/92 |
| 4,182,751 | 1/1980 | Ayme | 424/92 |
| 4,242,326 | 12/1980 | Sugawara et al. | 424/116 |

FOREIGN PATENT DOCUMENTS

| | | |
|---|---|---|
| 2092875 | 1/1972 | France . |
| 2130533 | 11/1972 | France . |
| 2218888 | 9/1974 | France . |
| 2268531 | 11/1975 | France . |
| 2269961 | 12/1975 | France . |
| 2283694 | 4/1976 | France . |
| 2374042 | 7/1978 | France . |
| 57091 | 1/1968 | Luxembourg . |

OTHER PUBLICATIONS

Prevot, A. R. et al., "Stimulation du systeme reticulo--endothelial", *C. R. Acad. Sciences*, Paris, 1963, 257 (Serie D), pp. 13–17.

Raynaud, M. et al., "Etude de L'Effet Immunostimulant de Diverses Especes de Corynebacteries Anaerobies et de leurs Fractions", *Ann. Inst. Pasteur*, 1972, pp. 695–700.

Prevot, A. R. et al., "Immunochemie.–Activite reticulostimulante des parois de Corynebacteries anaerobies", *C. R. Acad. Sc.*, Paris, 274 (Serie D), pp. 2256–2258 (April 1972).

Kouznetzova, B. et al., "Immunostimulating Activity of Whole Cells, Cell-Walls and Fractions of Anaerobic Corynebacteria", *Recent Results in Cancer Research*, pp. 275–293.

Migliore-Samour, D. et al., "A Hydrosoluble, Adjuvant-Active Mycobacterial Polysaccharide-Peptidoglycan. Preparation by a Simple Extraction Technique of the Bacterial Cells (Strain Peurois)", *Febs Letters*, vol. 25:2 (Sep. 1972), pp. 301–304.

Lallouette, P. et al., "Pouvoir Immunostimulant de fractions isolees de Corynebacterium Granulosum—Etudes sur la phagosytose et sur des tumeurs greffees de la souris"—*N.G.M.*25 (1975) 13, pp. 13–20.

(List continued on next page.)

*Primary Examiner*—Blondel Hazel
*Attorney, Agent, or Firm*—Browdy & Neimark

[57] ABSTRACT

The novel fractions extracted from aerobic bacteria are constituted either by whole cells, delipidized or undelipidized, or by insoluble particulate fractions or water-soluble fractions, extracted from delipidized whole cells. These fractions can be absorbed on inorganic gels to provide antitumoral, antibacterial and interferon inducing medicaments, suitable for intravenous administration.

9 Claims, 3 Drawing Figures

OTHER PUBLICATIONS

Bizzini, B. et al., "Isolement et caracterisation d'une fraction, dite fraction P40 a partir de Corynebacterium granulosum", *Medicine et Maladies Infectueuses*, 78:9, Tome VII, pp. 408–414.

Lallouette, P. et al., "Immunologie.—Effet antagoniste d'une isolee de Corynebacterium granulosum envers le pouvoir immunosuppresseur de la cyclophosphamide chez da Souris", *C.R. Sc.* Paris, t.283 Serie D, pp. 713–716 (9/27/1976).

Younger, J. S., "Interferon Production by Nonviral Stimuli of Microbial Origin", *The Journal of General Physiology*, 56:4, pp. 25–40 (Oct., 1970).

J. Vilcek, "Non-viral Inducers of Interferon Synthesis", *Virology Monograph, Interferon*, pp. 21–22, Editions Springer (1969).

Prevot, A. R. et al., "Bacteriologie.—Etude comparative du systeme reticuloendothelial par differentes souches de corynebacteries anaerobies et d'especes voisines", *C.R. Acad. Sc. Paris*, vol. 258, Group 13, pp. 4619–4621 (May 4, 1964).

Aebi, A. et al., "Sur les lipides de la souche humaine brevannes de Mycobacterium Tuberculosis", *Bull. Soc. Chim. Biol.*, 35:7, pp, 661–684 (1953).

*Chemical Abstracts*, vol. 86, No. 1, Jan. 3, 1977, p. 313, 3469w.

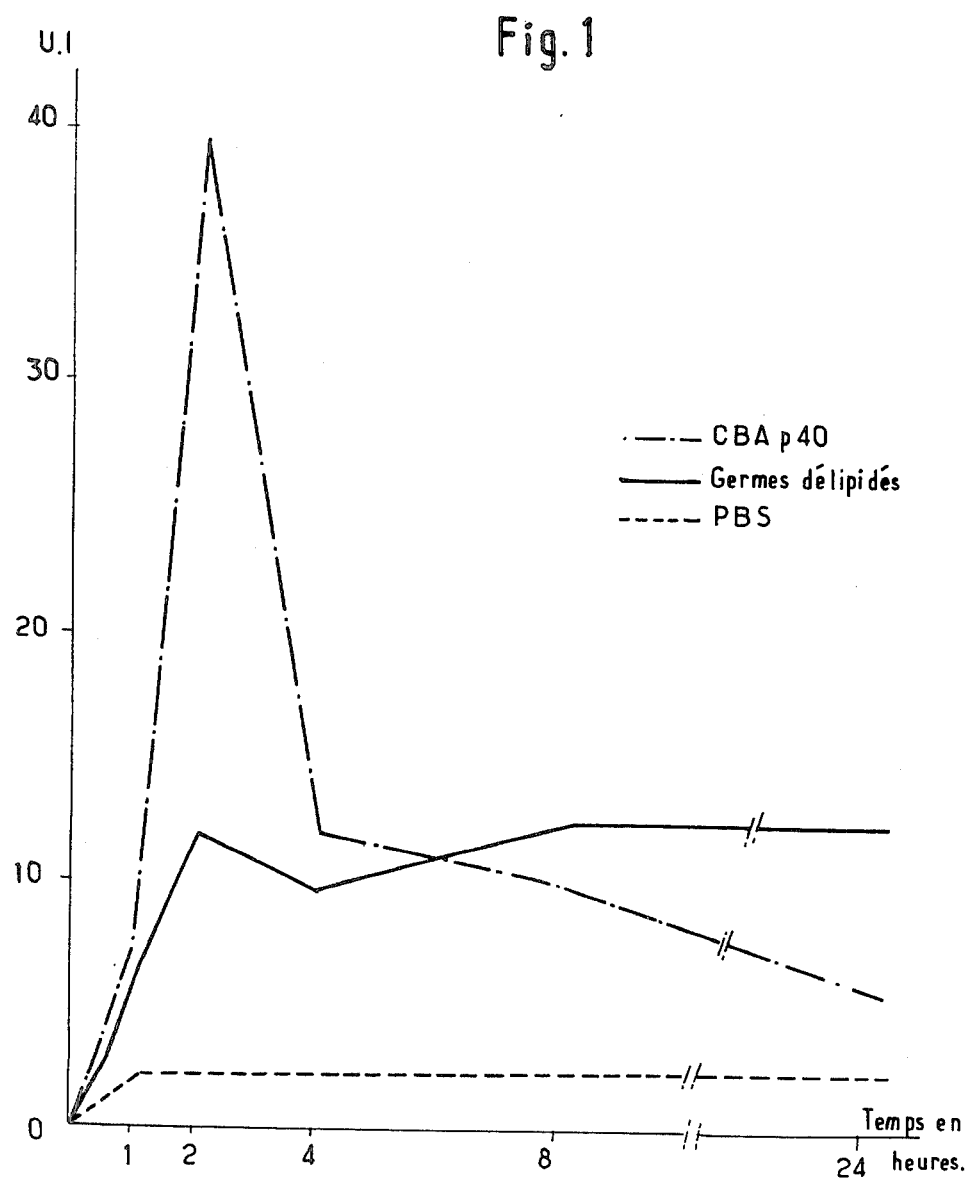

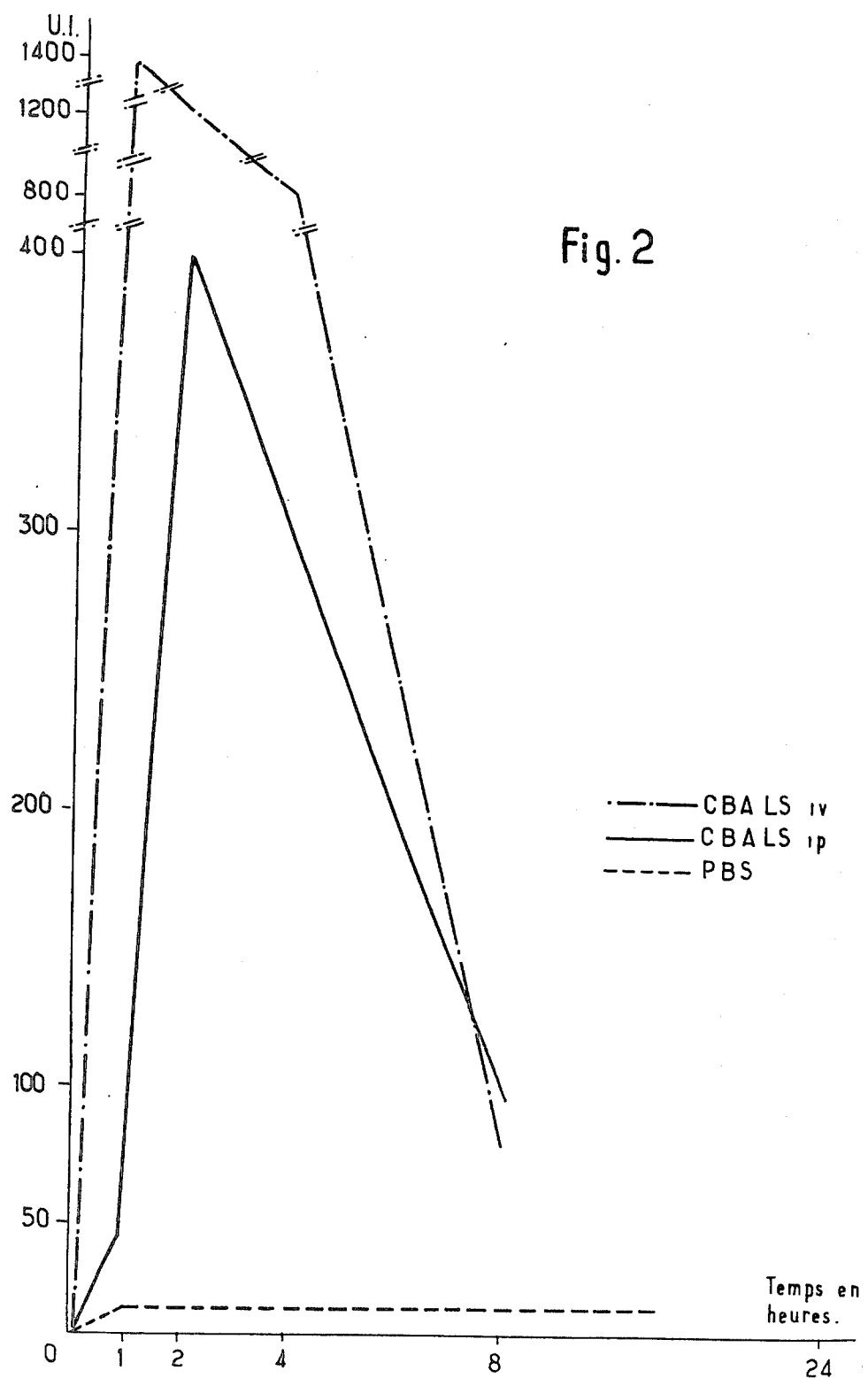

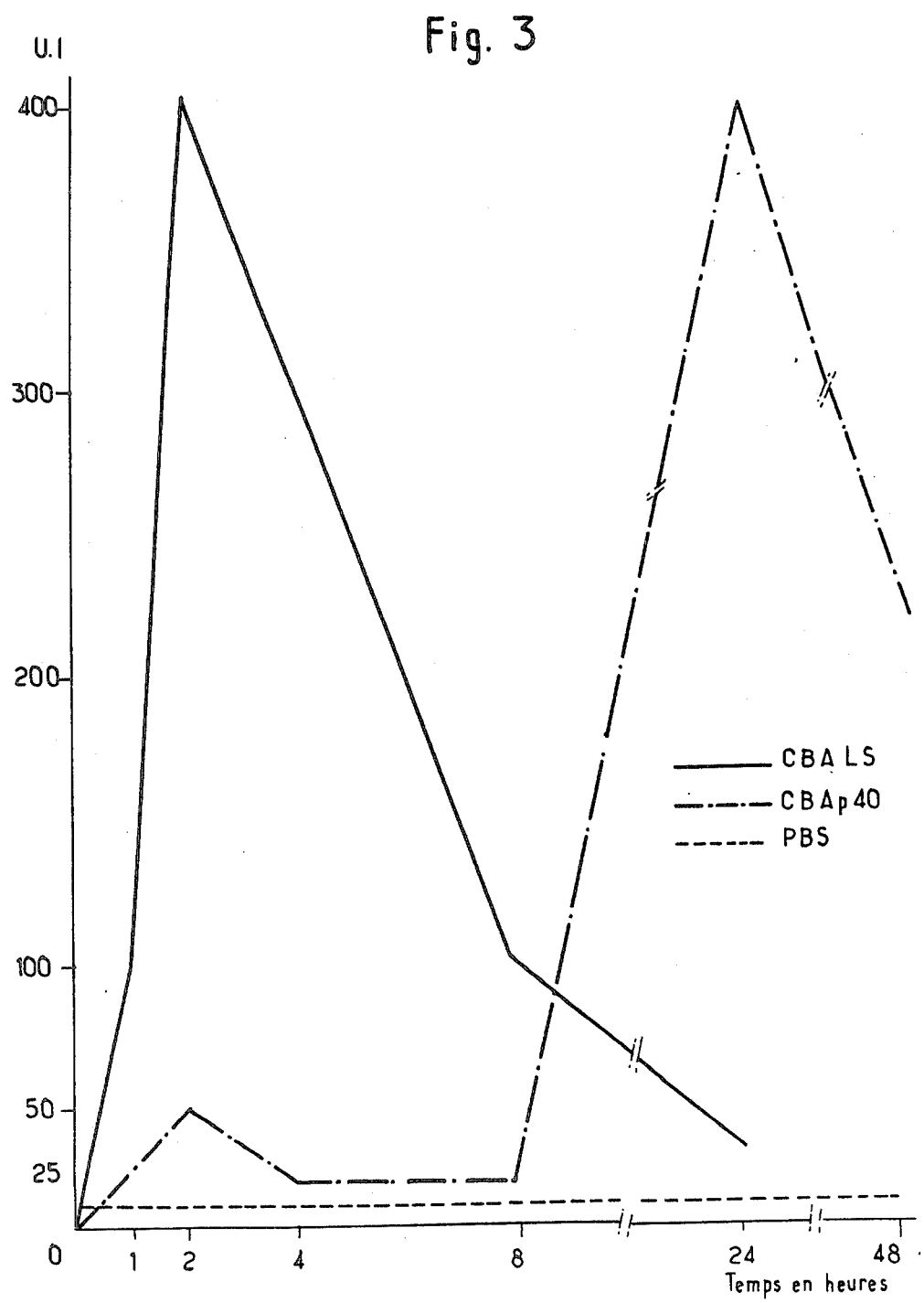

FRACTIONS EXTRACTED FROM AEROBIC BACTERIA, ENDOWED WITH ANTITUMORAL, ANTIBACTERIAL AND INTERFERON INDUCING PROPERTIES, AND PROCESS FOR THEIR PREPARATION

BACKGROUND OF THE INVENTION

1. Field of the Invention

The present invention relates to novel fractions extracted from aerobic bacteria, endowed with antitumoral, antibacterial and interferon inducing properties and to the process for their preparation.

2. Description of the Prior Art

Research investigations have established the immunostimulant and antitumoral power of killed microbial bodies of certain species of anaerobic Corynbacteriae [cf. notably A. R. PREVOT, B. N. HALPERN, F. BIOZZI, C. STIFFEL, D. MOUTON, J. C. MORARD, Y. BOUTHILLIER, C. DECREUSEFOND, C.R. Acad. Sci. (PARIS), 1963, 257 (Series D), 13]. Studies were then devoted to the isolation of active fractions from whole germs [cf. notably M. RAYNAUD, B. KOUZNETZOVA, B. BIZZINI and J. C. CHERMANN: "Study of the immunostimulant effect of various species of anaerobic Corynbacteriae and their fractions" Ann. Inst. PASTEUR, 1972, 122, 695–700; A. R. PREVOT, M. RAYNAUD, B. BIZZINI, J. C. CHERMANN, B. KOUZNETZOVA and F. SINOUSSI: "Reticulostimulant Activity of the walls of anaerobic Corynebacteriae "C.R. Acad. Sci. PARIS, t. 274 (Apr. 10, 1972)]; "B. KOUZNETZOVA and B. BIZZINI, J. C. CHERMANN, F. DEGRAND, A. PREVOT and M. RAYNAUD: "Recent results in cancer research" 1974, 47, 275–293 (Immunostimulating activity of whole cells, cellwalls and fractions of anaerobie corynebacteria)". D. MIGLIORE-SAMOUR and J. JOLLES [Febs Letters 25 no. 2 (1972) 301] have described the isolation from anaerobic Corynebacteriae, of a water-soluble fraction which has preserved the adjuvant power of the whole bacteria. Then P. LALLOUETTE, B. BIZZINI and M. RAYNAUD [N.G.M. 25(1975) 13], by applying the process of MIGLIORE-SAMOUR and JOLLES to the fractionation of *Corynebacterium granulosum*, found that the adjuvant and immunostimulant activity was associated not with the water-soluble fraction $S_{70}$, but with the particulate fraction $P_{40}$. The fraction $P_{40}$ isolated from *C. granulosum* was characterized chemically and biologically by B. BIZZINI, B. MARO and P. LALLOUETTE, [in Médecine et maladies infectieuses 78, no. 9, vol. VIII, pages 408–414 (isolation and characterisation of a so-called $P_{40}$ fraction from *Corynebacterium granulosum*)]. They established the particularly interesting curative action of the $P_{40}$ fraction on the P815 tumor in the mouse. On the other hand, P. LALLOUETTE, B. MARO, A. SCHWARTZ, B. BIZZINI (cf. C.R. Acad. Sci. (PARIS), 1976), showed that the $P_{40}$ fraction is capable of restoring and of increasing the immunogenic capacity of the formation of sheep anti-red blood cell antibodies in mice depressed by the injection of cyclophosphamide.

There exist in addition, a certain number of studies regarding the obtaining of interferon inducers, and notably the French MAES Pat. No. 2,092,875, relating to complexes inducing the formation of interferon and to the method for their preparation. These complexes are obtained by reacting a mono-, bi- or tricatenary nucleic acid with a dialkylaminoalkyl dextran in a weight ratio alkylaminoalkyldextran/nucleic acid less than 1/1 or with a synthetic polymer of aminoacids such as polylysine or polyornithine or indeed with basic natural proteins such as histone or lysozyme, or again with a synthetic cationic polyelectrolyte such as hexadimethrine bromide. French Pat. No. 2,130,533 in the name of The Kotasato Institute also describes a slightly toxic interferon inducer devoid of side effects, obtained from the supernatant liquor of a liquid culture medium of an organism of phase III, of phase II or of phase I of *Bordetella pertussis*, or from a fraction obtained by disintegration of the protoplasm of an organism of phase III, of phase II or of phase I of *Bordetella pertussis* and subsequent separation of the lipopolysaccharide endotoxin and of the O-antigen of the somatic components of the bacteria. This patent sets out in addition the state of the art in prior publications [Julius S. YOUNGER, Journal General Physiology, 56 (1), Part 2, pages 25–40 (1970) and J. VILCEK, Virology Monograph, Vol. 6, Interferon, Editions SPRINGER, 1969, P. 21–22] which describe interferon inducers for the prevention of viral infectious diseases, such as various viruses, bacteria (in particular Gram negative bacteria), the lipopolysaccharide endotoxins of these bacteria, metabolic products of molds, double-helix polysaccharides and ribonucleic acids, all considered as toxic and inducing undesirable side actions. The UPJOHN American U.S. Pat. No. 4,007,086 describes, for its part, a process for interferon production in vitro which consists of subjecting human or animal interferon producing cells to ultra-violet radiation of 50 ergs/mm$^2$ to 2,500 ergs/mm$^2$, before, at the same time or after the addition to these cells of a non-viral interferon inducer. The interferon inducer applied according to this Patent may be an endotoxin, a bacterium, a trachomatous conjunctivity agent, a mycoplasm, a protozoan, a rickettsia, a synthetic polymer, a mitogen, a polysaccharide, an antibiotic, an interferon inducer of low molecular weight such as tilorone hydrochloride, natural and synthetic nucleic acids, and notably mono- or di-catenary ribonucleic acids and their complexes with polysaccharides and other substances.

The possibility of having availabe a non-toxic interferon inducer devoid of side effects is all the more important in that interferon is only produced in the presence of interferon inducers. Now, interferon, which is a protein which appears in the blood or the organs of animals or in tissue culture media when the latter are subjected to the action of an interferon inducer, prevents or attenuates viral diseases.

It is an object of the present invention to provide a novel agent having at the same time, adjuvant properties, immunostimulant properties, antibacterial properties, and interferon inducing properties.

As has been shown above, the adjuvant and immunostimulant power of anaerobic Corynebacteriae has been amply demonstrated. On the other hand, tests carried out on known aerobic Corynebacteriae have shown that the latter are devoid of adjuvant and immunostimulant properties (Comptes-rendus de l'Academie des Sciences Paris 1964, vol. 258, p. 4619–4621).

Applicants have isolated from the sputum of a patient afflicted with generalized cancer with extensive pulmonary and mesenteric metastases, a new Corynebacterium aerobe, in pure culture directly.

The culture of this Corynebacterium aerobe has been carried out according to the usual techniques, either in a glass flask of 5 liters capacity, or in a stirred fermenter of 50 liters capacity, or again on a solid medium.

The bacterium was cultivated on different media: ordinary broth, ordinary gelose, ordinary broth enriched with Bactopeptone and with yeast extract.

The characteristics of the bacterium isolated are those of an aerobic of the genus Corynebacterium, namely:

Morphology: slender rod-shaped bacilli, rare forms of V-oriented club shapes, or in heaps, or in comb shapes. Gram +, having metachromatic corpuscles Culture:
  (a) On ordinary broth, clouds, then deposition and formation of a fog at the surface after some days;
  (b) On ordinary gelose: opaque colonies appearing in 24 hours, widening further assuming a yellowish color.

Energizing metabolism:
  Nitrate + ($NO_3$-$NO_2$+1)
  Urease +
  Catalase +
  Methyl red +

Biochemical characteristics:
  Dextrin: 1.2±3
  Glucose +
  Levulose +

This germ, which has not been identifiable with any known species, has been denoted by the name *Corynebacterium catarrhalis* by Applicants and has been deposited in the National Collection of Microorganism Cultures held by the PASTEUR INSTITUTE, on the date Feb. 21, 1980, under the number I-116.

SUMMARY OF THE INVENTION

According to the present invention there are provided active fractions, characterized in that they are obtained from strains of aerobic bacteria.

According an advantageous embodiment of the invention, said active fractions are constituted by washed whole cells of aerobic bacteria.

According to another advantageous embodiment of the invention, said active fractions are constituted by delipidized whole cells of aerobic bacteria.

According to another advantageous embodiment of the invention, said active fractions are constituted by insoluble particulate fractions extracted from delipidized whole cells of aerobic bacteria.

In accordance with the invention, said active fractions are constituted by washed or delipidized whole cells of aerobic Corynebacteriae, or by insoluble particulate fractions or water-soluble fractions, obtained by gentle extraction of delipidized whole cells of Corynebacterium aerobes.

In accordance with a preferred feature of the invention, said active fractions are constituted by washed or delipidized whole cells of *Corynebacterium catarrhalis*, or by insoluble particulate fractions or water-soluble fractions, obtained by gentle extraction of delipidized whole cells of *Corynebacterium catarrhalis*, which is the novel strain of aerobic Corynebacterium isolated by Applicants, identified above.

In accordance with the invention, the above-said active fractions are put into a form enabling their administration by the intravenous route, in which the active fractions constituted by washed or delipidized whole cells of aerobic bacteria, notably of Corynebacterium aerobes and, specifically, *Corynebacterium catarrhalis*, have adjuvant, immunostimulant and antibacterial properties, the active fractions constituted by insoluble particulate fractions extracted from said delipidized whole bacterial cells having adjuvant, immunostimulant, antibacterial and interferon inducing properties and the water-soluble fractions extracted from said delipidized whole bacterial cells, having interferon inducing properties.

Again according to the invention, the above-said active fractions are put into a form enabling their administration by the sub-cutaneous route as anti-infectious agents, whether they relate to active fractions constituted by washed whole cells or by delipidized whole cells of aerobic bacteria, or indeed by particulate fractions obtained by gentle extraction of delipidized whole cells or again by water-soluble fractions obtained by gentle extraction of delipidized whole cells.

According to a preferred modality of this embodiment, the active fractions of the anti-infectious agent according to the present invention, are made suitable for administration by the sub-cutaneous route, by absorbing them on a mineral gel.

In accordance with the present invention, the mineral gel on which the active fractions of aerobic bacteria are absorbed to enable their administration by the subcutaneous route, is selected from the group which comprises notably calcium phosphate gels and aluminum hydroxide gels.

It is also an object of the present invention to provide a process for the preparation of active fractions in accordance with the foregoing features, which process is essentially characterized in that a strain of aerobic bacteria, notably of aerobic Corynebacteriae and, specifically *Corynebacterium catarrhalis*, is cultivated in a suitable culture medium, and under pH conditions close to neutrality, and in that the cultured bacteria are harvested, by separation from the culture medium and notably by centrifugation, at the commencement of the stationary phase, and then the bacteria are washed.

According to an advantageous modality of the process according to the invention, the washed whole cells of said bacteria, are subjected to a delipidization treatment, for example, by applying the delipidization method described by A. AEBI and Alia [Bull. Soc. Chim. Biol. 35, 661 (1953)], which treatment is if necessary followed by a gentle extraction treatment applied to the delipidized cells, as that described in the Patent ANVAR No. 74 15570 dated May 6, 1974 by P. JOLLES and D. MIGLIORE-SAMOUR, which permits the collection of an insoluble particulate fraction and a soluble particulate fraction.

According to another advantageous embodiment of the process according to the invention, the washed or delipidized whole cells or the insoluble or water-soluble fractions obtained by extractions of delipidized whole cells, are put into form enabling their administration by the subcutaneous route, by absorbing them on a mineral gel selected from the group which comprises notably calcium phosphate gels and aluminum hydroxide gels.

According to an advantageous modality of this embodiment of the process, the adsorption of the delipidized or undelipidized whole cells, or of the insoluble particulate fractions or of the water-soluble fractions which constitute the active fractions of said medicaments on calcium phophate gel is carried out by the addition, with stirring, of a predetermined volume of $CaCl_2$, 0.07M, to an equal volume of suspension of said cells or insoluble particulate fractions or of water soluble fractions, (0.07M disodium phosphate solution), the pH of the mixture being then adjusted to neutrality by the addition of 0.1NaOH.

According to another advantageous modality of this embodiment of the process,—in the course of a first step, a preformed gel is prepared by fixing volume to volume of a 0.07M disodium phosphate solution and 0.07M $CaCl_2$ solution, adjustment of the mixture of about pH 7 by the addition of 0.1N NaOH, sedimentation of the gel formed and washing by an isotonic solution of sodium chloride;—in the course of a second step, there is added to the washed preformed gel, the active fraction to be adsorbed—suspension of whole bacteria or of insoluble particulate fractions or water soluble fraction solutions—, then the mixture is stirred for a sufficient time to enable the adsorption of the product on the gel, after which the finished product is centrifuged and washed by an isotonic NaCl solution.

In accordance with yet another modality of this embodiment, the active fractions of said medicaments—suspension of whole bacteria or of insoluble particulate fractions or water soluble fractions—are adsorbed on aluminum hydroxide gel by mixing aluminum hydroxide gel and said active fractions in proportions such that the final mixture contains 1.365 mg of $Al(OH)_3$/ml and 1 mg of active fraction/ml.

DETAILED DESCRIPTION OF PREFERRED EMBODIMENTS

The invention will be better understood with the aid of the additional description which follows, which refers on the one hand to examples of the preparation of active fractions according to the invention, and on the other hand to accounts of pharmacological experiments designed to demonstrate the adjuvant, immunostimulant and antibacterial power and the interferon inducing activity of the active fractions according to the invention.

It must however be well understood that these examples and accounts of experiments are given purely by way of illustration of the invention of which they are not to be considered as constituting a limitation in any way.

EXAMPLE I

Preparation of an active fraction constituted by washed whole cells.

*Corynebacterium catarrhalis* was cultivated in a fermenter in amounts of 50 liters. The culture medium was constituted by a meat broth supplemented with 5 g/liter of Bactopeptone and 2 g/liter of yeast extract. The pH was adjusted to 7.4. The bacteria were collected by centrifugation of the culture at the beginning of the stationary phase. The bacteria were washed with two repetitions resuspending them in distilled water and centrifuging them.

The washed bacteria, denoted by the sign BL, can be used as such as an anti-infectious agent adapted for administration by the intravenous route.

EXAMPLE 2

Preparation of an active fraction constituted by delipidized whole cells.

Cells of a *Corynebacterium catarrhalis* culture were subjected to a delipidizing process according to the method described by A. AEBI and Coll., Bull. Soc. Chim. Biol. 35, 661 (1953).

EXAMPLE 3

Preparation of active fractions constituted respectively by an insoluble fraction and by a water soluble fraction extracted from delipidized whole cells. 50 g of delipidized whole cells obtained as described in Example 2 above, were fractionated by applying the method of D. MIGLIORE-SAMOUR and Alia mentioned in the preamble which consists of grinding and homogenizing said cells in 250 cm$^3$ of water containing a non-ionic detergent of the type "NP-40", in a grinder of the "OMNI MIXER SORVALL" type.

After stirring for 5 hours at the temperature of the laboratory, followed by centrifugation for 15 minutes at 4° C. (2,000 g), the supernatant layer was heated to 80° C., then saturated ammonium sulfate solution was added so as to obtain a solution with 40% saturation.

It was kept for 12 hours at 4° C., then centrifuged for 15 minutes at 4° C. (at 4,000 g), and a precipitate collected constituted by the fraction CBAp40.

The water soluble fraction present in the supernatant liquor on precipitation of the fraction CBAp40 is denoted by the fraction name LS.

The precipitate containing the fraction CBAp40, as well as the supernatant liquor from centrifugation, were dialysed to remove all traces of ammonium sulfate. The products were finally lyophilized.

EXAMPLE 4

Preparation of active fractions adsorbed on a calcium phosphate gel.

Whole cells as well as insoluble particulate fractions and water soluble fractions were adsorbed on calcium phosphate gel by proceding as follows:
the adsorption on the calcium phosphate gel was effected by the addition, with stirring, to a predetermined volume of bacteria suspension or of CBAp40 or of CBA-LS in 0.04M $Na_2HPO_4$, of an equal volume of 0.07M $CaCl_2$. The pH of the mixture was then adjusted to neutrality by the addition of 0.1N NaOH.

EXAMPLE 5

Preparation of active fractions adsorbed on a calcium phosphate gel.

100 ml of 0.07M disodium phosphate solution and 100 ml of 0.07M $CaCl_2$ solution were mixed. The pH was adjusted to 7 by the addition of 0.1N NaOH. The gel formed was sedimented by centrifugation and washed twice with an isotonic NaCl solution.

To this preformed and washed gel, was added the product to be adsorbed which can be the solution of CBA-LS in an isotonic NaCl or a bacteria suspension of CBAp40 in isotonic NaCl.

The mixture was stirred for 30 minutes with a magnetic stirrer so as to enable the adsorption of the product. This gel was centrifuged and washed with an isotonic NaCl.

EXAMPLE 6

Preparation of active fractions adsorbed on aluminum hydroxide gel.

The adsorption on the aluminum hydroxide gel was obtained by mixing amounts of "ALHYDROGEL" (Superfos Export Co.) and of the product subjected to experiment, in proportions such that the final mixture contained 1.365 mg of $Al(OH)_3$/ml and 1 mg of product subjected to experimentation/ml.

Account of pharmacological experiments

1. The adjuvant and immunostimulant power of the delipidized cellular fractions and of the CBAp40 fractions were demonstrated by proceding as follows:
   Animals: for this study, male B6 D2 F1 mice of 18–20 g were used supplied from IFFA-CREDO.
   Tumor: a Lewis tumor (3LL) was grafted by intramuscular injection of $10^5$ or $10^6$ viable cells, according to the experiment in a volume of 0.2 ml into the right rear paw. The development of the tumor and the mortality were followed daily.
   Treatment: this was done by a single intravenous injection of 250 μg of the fraction CBAp40, in a volume of 0.5 ml, either 2, 3 or 4 days before, or the same day, or 3, 6, 9 or 10 days after the tumoral graft. For comparison, batches of mice received 250 μg or 500 μg of delipidized whole cells or of LS fraction, according to the same modalities.

Statistical analysis of the results: the results that were analysed either by the Student test when the mortality was 100% of the animals at the end of the experiment (Table 1) or by the $X^2$ test, when a certain percentage of animals survived at the end of the experiment (Tables 2, 3 and 4).

RESULTS

The results of the experiments are reported in the Tables 1, 2, 3 and 4. In addition, in Table 1 are also shown the percentage increase of the lifespan of the animals (ILS%), and the mean survival time (MST).

Two types of experiments must be distinguished: those summarized in Tables 1 and 4 in which 100% mortality in the control animals is observed, and those summarized in Tables 2 and 3 in which a certain percentage of controls survive. In the latter case, it is justified to assume that the situation is one of residual disease.

TABLE 1

Effect on the development of the Lewis tumor in the mouse of the CBAp40 fraction injected before, at the same time or after the tumoral graft with $10^6$ cells by the intramuscular route

| Immuno-stimulant | Route of inoculation | dose μg | Day of inoculation | Number of animals | Number surviving at the 60th day | Mouse mortality day | Death interval | ILS % | MST | Test t |
|---|---|---|---|---|---|---|---|---|---|---|
| CBAp40 | I.V. | 250 | −2 | 6 | 0 | 24, 28, 28, 28, 32, 39 | 24–39 | 3.5 | 29.8 | $9.0 > p > 0.5$ |
| CBAp40 | I.V. | 250 | 0 | 6 | 0 | 17, 24, 27, 27, 30, 38 | 17–38 | — | 27.2 | $0.9 > p > 0.5$ |
| CBAp40 | I.V. | 250 | 3 | 6 | 0 | 26, 26, 30, 31, 32, 38 | 26–38 | 5.9 | 30.5 | $0.5 > p > 0.3$ |
| CBAp40 | I.V. | 250 | 6 | 6 | 2 | 34, 35, 36, 39 | 34–39 | 25 | 36 | $0.01 > p > 0.001$ |
| CBAp40 | I.V. | 250 | 10 | 6 | 0 | 28, 28, 30, 34, 36, 39 | 28–39 | 12.8 | 32.5 | $0.05 > p > 0.02$ |
| PBS | I.V. | 0.5 ml | 0 | 6 | 0 | 26, 28, 28, 28, 30, 33 | 26–33 | — | 28.8 | — |

TABLE 2

Effect on the development of the Lewis tumor in the mouse of the CBAp40 fraction injected before, at the same time or after tumoral graft with $10^5$ cells by the intramuscular route

| Immuno-stimulant | Route of inoculation | Dose μg | Day of inoculation | Number of animals | Number surviving at the 60th day | Mouse mortality day | Test $X^2$ |
|---|---|---|---|---|---|---|---|
| CBAp40 | I.V. | 250 | −4 | 10 | 7 | 31, 45, 55 | $0.1 > p > 0.05$ |
| CBAp40 | I.V. | 250 | 0 | 10 | 7 | 29, 43, 48 | $0.1 > p > 0.05$ |
| CBAp40 | I.V. | 250 | 3 | 10 | 8 | 45, 48 | $0.05 > p > 0.02$ |
| CBAp40 | I.V. | 250 | 6 | 10 | 10 | — | $p = 0.001$ |
| CBAp40 | I.V. | 250 | 9 | 10 | 8 | 31, 32 | $0.05 > p > 0.02$ |
| PBS | I.V. | 0.5 ml | 0 | 10 | 3 | 29, 31, 34, 34, 35, 36, 52 | — |

TABLE 3

Effect on the development of the Lewis tumor in the mouse of delipidized germs (GD) injected 3, 6 and 9 days after the tumoral graft with $10^5$ cells by the intramuscular route

| Immuno-stimulant | Route of inoculation | Dose g | Day of inoculation | Number of animals | Number surviving at the 60th day | Mouse mortality day | Test $X^2$ |
|---|---|---|---|---|---|---|---|
| GD | I.V. | 500 | 3 | 10 | 7 | 38, 45, 59 | $0.1 > p > 0.05$ |
| GD | I.V. | 500 | 6 | 10 | 9 | 31 | $0.01 > p > 0.001$ |
| GD | I.V. | 500 | 9 | 10 | 7 | 38, 41, 43 | $0.1 > p > 0.05$ |
| PBS | I.V. | 0.5 ml | 6 | 10 | 3 | 29, 31, 34, 34, 35, 36, 52 | — |

TABLE 4

Effect compared with the development of the Lewis tumor in the mouse, of delipidized germs (GD) and of the supernatant liquor (LS) of the precipitation of the CBAp40 fraction injected 6 days after the tumoral graft with $10^6$ cells by the intramuscular route

| Immuno-stimulant | Route of inoculation | Dose g | Day of inoculation | Number of animals | Number of surviving at the 60th day | Mouse mortality day | Test $X^2$ |
|---|---|---|---|---|---|---|---|
| GD | I.V. | 500 | 6 | 10 | 8 | 28, 32 | $P < 0.001$ |
| GD | I.V. | 250 | 6 | 10 | 3 | 32, 37, 40 40, 40, 41 44 | $0.1 > p > 0.05$ |
| LS | I.V. | 250 | 6 | 10 | 2 | 27, 30, 30 31, 32, 34, 40, 41 | $0.2 > p > 0.1$ |
| PBS | I.V. | 0.5 ml | 6 | 10 | 0 | 21, 23, 26 27, 30, 30 30, 32, 34, 51 | — |

It is brought out from Tables 1 and 2 above that the CBAp40 fraction injected four days or two days before, the same day or three days after the tumoral graft does not influence the development of the tumor significantly. On the contrary, injected six days or ten days after the tumoral graft, the CBAp40 fraction exerts a distinct inhibiting effect on the growth of the tumor. This effect is more pronounced when the treatment is instituted six days after the graft of the tumor.

In the situation of residual disease (Table 2), the CBAp40 fraction injected six days after the tumoral graft leads to the definite survival of all the treated animals.

In the comparative tests (Table 4), the delipidized whole cells (GD), administered in the dose of 500 µg per mouse, six days after the tumoral graft, exerted a highly significant antitumoral effect. The inhibiting effect on the tumoral development was not increased (Table 3), contrary to what was observed with the fraction CBAp40 (Table 2), in the situation of residual disease.

Finally, at the dose of 250 µg per mouse, the fraction LS administered six days after the tumoral graft, does not exert any significant inhibiting effect on the growth of the tumor (Table 4).

In conclusion, the results reported in the foregoing demonstrate that the aerobic Corynebacterium used in the above-summarized experiments, exerted a distinct inhibiting effect on the development of a Lewis tumor. On the other hand, the CBAp40 fraction isolated from C. catarrhalis by JOLLES & MIGLIORE-SAMOUR process used for producing the P40 fraction from C. granulosum, showed itself endowed, like the last fraction, with antitumoral power.

Immunostimulating power of Corynebacterium catarrhalis has been demonstated by using bacteria completely killed by heating. The bacteria were administered to the mouse (SWISS of 18 g) by the sub-cutaneous or intravenous route at a dose of 200 to 400 µg. The infection was produced by injecting into each mouse a dose 5 or 10 $LD_{50}$ of E coli, K pneumoniae or L. monocytogenes bacteria. When a dose of 5 $LD_{50}$ of infecting bacteria was used, 95 to 100% of the mice were protected by Corynebacterium catarrhalis. The protection was of the order of 80 to 100% when the infection was carried out with 10 $LD_{50}$.

2. Determination of the interferon inducing activity in two fractions isolated from Corynebacterium catarrhalis (CBAp40 and CBA LS).

Equipment and methods

Fractions: two fractions of C. catarrhalis were tested, nanely the insoluble fraction CBAp40 and the soluble fraction CBA LS (representing the residual product of the preparation of the CBAp40 fraction) and the delipidized germs were used as a reference.

Animals: SWISS mice (Rennemoulin) of 20 g body weight. batches of 10 mice were used for each determination.

Doses and inoculation routes: the products were injected at the dose of 250 g, (lyophilized products resuspended or redissolved in PBS in a volume of 0.5 ml) either by the intravenous route (I.V.) or by the intraperitoneal route (I.P.).

The control mice received 0.5 ml PBS by the I.V. or I.P. route.

Titration: blood samples were taken by the retroorbital route 1, 2, 4, 8, 24 and 48 hours after the injection of the fractions.

A serum-standard titrating 60,000 I.U. was used as a reference for the calculation of the activity in I.U.

The continuous line of cells of mouse testicles L929 was used for the titration. The cells were cultivated in modified GLASGOW medium, containing 10% of foetal calf serum (SVF). The titration was carried out on plastic plates (NUNCLON Microtest). Each cup received 0.05 ml of serum to be tested diluted from 1/5 to 1/360 or the reference serum diluted from 1/400 to 1/12600. In each cup, was then distributed $3 \cdot 10^4$ cells in a volume of 0.05 ml. The cells were cultivated for 24 hours at 37° C. in the presence of air containing 5% $CO_2$. The medium contained in the cups was then discarded and it was replaced by virus of vesicular stomatitis (VSV) (one particle per cell, namely $3 \times 10^4$ viral particles) in a volume of 0.1 ml. After further incubation of 18 hours, the $DCT_{50}$ was established for the virus control, the serum-standard and for the serum to be tested (animals treated with fractions or PBS). The number of units was calculated by comparison with the reference serum.

RESULTS

The results are reported in Table 5 below and, in the form of graphs, in attached FIGS. 1, 2, and 3.

The results reproduced in the FIGS. 1, 2, and 3 were obtained with the batch no. 1 of CBAp40, whilst those reproduced in FIG. 3 were obtained with batch no 2.

FIG. 1 shows graphically the interferon inducing activity of the CBAp40 fraction and of the delipidized cells, administered by the I.V. route at the dose of 200 µg per mouse.

FIG. 2 shows graphically the interferon inducing activity of the the CBA LS fraction administered by the I.V. and I.P. route at the dose of 250 μg per mouse, and FIG. 3 shows graphically the interferon inducing activity of the CBAp40 fraction and of the CBA LS fraction administered by the I.P. route at the dose of 200 μg per mouse.

FIG. 1 shows that the interferon production is induced at the second hour by the CPAp40 and at a lower level by the delipidized germs. For the CBAp40, a considerable decrease from the 4th hour is observed, whilst with the delipidized germs the level varies little.

FIG. 2 summarizes the results obtained with the CBA LS soluble fraction. The production of a high interferon level from the 1st hour is observed if the product is administered by the I.V. route, and from the 2nd hour if the product is injected by the I.P. route. A considerable drop of the interferon level from the 4th hour is observed.

The results of the comparison of the interferon inducing activity of CPAp40 and CBA LS are summarized in FIG. 3. The CBA fraction is interferon inducing at the 1st hour with an activity maximum reached at the 2nd hour (400 I.U.). On the other hand, the CBAp40 fraction only permits interferon production at a low level at the 2nd hour, but at a high level at the 24th hour (400 I.U.).

In the control mice (PBS), the presence of interferon was not observed.

The results reported above indicate that the delipidized whole bacterial cells of C. catarrhalis are practically devoid of interferon inducing activity (cf. FIG. 1). On the contrary, both the CBAp40 fraction and the CBA LS fraction are capable of inducing interferon formation. However, these two fractions must act differently, since the appearance kinetics of the interferon is different. With the CBAp40 fraction, the activity maximum is reached at the 24th hour (cf. FIG. 3), whereas for the CBS LS fraction, the activity maximum is observed towards the 1st-2nd hour (cf. FIGS. 2 and 3).

On the other hand, with the CBA LS fraction an activity difference as a function of the administrative route is noted, the I.P. route being more effective than the I.V. route, and an activity difference from one batch to the other, lot I (FIG. 2) and lot II (FIG. 3).

As is known, different species of anaerobic Corynebacteriae are established to be powerful stimulating agents of the reticulo-endothelial system. In addition, among anaerobic Corynebacteriae, *Corynebacterium parvum* and *Corynebacterium granulosum* are established to increase resistance to various bacterial infections. As indicated in the preamble, the fractionation of whole cells of anerobic Corynebacteriae has given rise to fractions which have the immunoadjuvant activities of the intact bacterium. It has been demonstrated by one of Applicants of the present Patent Application that an insoluble particulate fraction isolated from *Corynebacterium granulosum* denoted by the fraction named P40, has a powerful immunostimulant and adjuvant activity.

Contrary to this, a certain number of investigators have demonstrated that aerobic Corynebacteriae are either devoid of immunostimulating and adjuvant activity, or indeed have a very low activity of this type.

As indicated above, the fractions extracted from delipidized whole cells of Corynebacterium, have considerable activities as interferon inducers.

To demonstrate the possibilities of use in therapeutics of the fractions so isolated, for the preventional treatment of infections in patients having an immunitary deficiency, Applicants have continued their research in order to determine whether whole cells or fractions of *Corynebacterium catarrhalis* could increase the resistance of mice to *Listeria monocytogenes*.

As is known, *Listeria monocytogenes* is a non-sporulated aerobic germ which is the agent of an infectious disease common to man and to animals, listeriosis, which can assume particularly serious forms.

Applicants have demonstrated the anti-infectious action exerted by *Corynebacterium catarrhalis* by showing the protective action exerted by the letter against infection induced by *Listeria monocytogenes* in the mouse, by proceeding as follows:

1. As animals, there were used SWISS female mice weighing from 17 to 19 g. The animals were subjected to the usual laboratory feeding and received water freely.
2. The products subjected to the experiments were injected at a dose of 400 μg (dry weight) in physiological serum.
   (a) The injections were carried out by the intravenous route (I.V.) as regards the non-absorbed products, in a volume of 0.2 ml,
   (b) the injections were carried out by the sub-cutaneous route (S.C.) for the absorbed products, in a volume of 0.4 ml.
3. Into control mice were injected:
   either physiological serum by the intravenous route, or a calcium phosphate or aluminum hydroxide gel not containing the products subjected to experiment, by the sub-cutaneous route.

Infection

The mice were infected by *Listeria mono-cytogenes* obtained by cultivation for 18 hours of the strain 1150,

TABLE 5

Interferon inducing activity of the CBAp40 fraction, CBA LS and delipidized germs administered by the I.V. or I.P. route to mice of 20 g.

| FIGS. No. | Products | Dose μg | Route of administration | Interferon International Units HOURS | | | | | |
|---|---|---|---|---|---|---|---|---|---|
| | | | | 1 | 2 | 4 | 8 | 24 | 48 |
| 1 | CBAp40 | 200 | I.V. | 8 | 38.4 | 12.8 | 9.6 | 6.4 | |
| | Delipidized germs | 200 | I.V. | 6.4 | 12.8 | 9.6 | 12.8 | 12.8 | |
| | P.B.S. | 0.5 ml | I.V. | 3.2 | 3.2 | 3.2 | 3.2 | 3.2 | |
| 2 | CBA LS | 250 | I.V. | 1400 | 1200 | 800 | 80 | | |
| | CBA LS | 250 | I.P. | 50 | 400 | 300 | 100 | | |
| | P.B.S. | 0.5 ml | I.P. | 3.2 | 3.2 | 3.2 | 3.2 | | |
| 3 | CBAp40 | 250 | I.P. | 25 | 50 | 25 | 25 | 400 | 100 |
| | CBA LS | 250 | I.P. | 100 | 400 | 300 | 100 | 40 | |
| | P.B.S. | 0.50 ml | I.P. | 3.2 | 3.2 | 3.2 | 3.2 | 3.2 | | by intravenous injection at a suitable dilution (3-4 MLD); the injection took place six days after the mice had received one of the products subject to experiment.

This dose of *Listeria monocytogenes* produced 100% mortality in the control mice in the space of 24 to 96 hours. The deaths were recorded for 10 days.

In certain cases, the mice were again infected 75 days after the first injection, by the injection by the intravanous route of 20 MLD of *Listeria monocytogenes*.

Results

The results obtained by previously treating mice by the intravenous route, either by BL, or by BD, are combined in Table 6 below.

TABLE 6

Protective effect of prior treatment by the intravenous route of mice by means of whole cells, either washed (BL), or delipidized (BD), of Corynebacterium catarrhalis, against infection by Listeria monocytogenes

| Products | Death supervening at day | | | | | | | | | | Ratio of deaths |
|---|---|---|---|---|---|---|---|---|---|---|---|
| | 1 | 2 | 3 | 4 | 5 | 6 | 7 | 8 | 9 | 10 | |
| BL | 0 | 0 | 0 | 0 | 0 | 2 | 0 | 0 | 0 | 0 | 2/8 |
| BD | 0 | 0 | 0 | 0 | 0 | 0 | 0 | 0 | 0 | 0 | 0/10 |
| Controls | 10 | 0 | 0 | 0 | 0 | 0 | 0 | 0 | 0 | 0 | 10/10 |

It is seen from Table 6 above that 100% mortality was recorded in the control mice in the space of 24 hours after injection by *Listeria monocytogenes*.

Contrary to this, a high degree of protection (75-80% of the mice were protected) was obtained when the mice had been stimulated by the intravenous injection, either of BL, or of BD, five days before being injected with *Listeria monocytogenes*. These results show clearly that a prior treatment of the mice by the intravenous route with whole cells of *Corynebacterium catarrhalis* can effectively increase their resistance to *Listeria monocytogenes*.

The results obtained when the mice were pretreated treated sub-cutaneously, either with BL, or with BD previously adsorbed either on a calcium phosphate gel, or on an aluminum hydroxide gel, are assembled in Table 7 which follows.

TABLE 7

Protective effect against infection by Listeria monocytogenes of a prior subcutaneous treatment in mice, either with washed whole cells (BL) or delipidized whole cells (BD) of Corynebacterium catarrhalis adsorbed either on a calcium phosphate gel (CP), or on an aluminum hydroxide gel (AH).

| Products | Death supervening at day | | | | | | | | | | Ratio of deaths |
|---|---|---|---|---|---|---|---|---|---|---|---|
| | 1 | 2 | 3 | 4 | 5 | 6 | 7 | 8 | 9 | 10 | |
| BL (CP) | 0 | 0 | 0 | 0 | 0 | 0 | 0 | 0 | 0 | 0 | 0/10 |
| BL (AH) | 0 | 0 | 0 | 0 | 0 | 0 | 0 | 0 | 0 | 0 | 0/10 |
| BD (CP) | 0 | 0 | 0 | 0 | 0 | 0 | 0 | 0 | 0 | 0 | 0/10 |
| BD (AH) | 0 | 0 | 0 | 0 | 0 | 0 | 0 | 0 | 0 | 0 | 0/10 |
| Physiological serum | 10 | 0 | 0 | 0 | 0 | 0 | 0 | 0 | 0 | 0 | 10/10 |
| (CP) alone | 0 | 0 | 0 | 4 | 4 | 0 | 0 | 0 | 0 | 0 | 8/8 |
| (AH) alone | 0 | 0 | 0 | 4 | 2 | 0 | 0 | 0 | 0 | 0 | 6/8 |

In the experiments taken into account in Table 7 above, it has also been verified that the mortality of the mice infected by *Listeria monocytogenes* in the space of 24 hours was 100%. The results presented in this Table show, in addition, that the pre-treatment of mice sub-cutaneously by adsorbed products is extremely effective since it permits 100% protection to be obtained against injection of animals by *Listeria monocytogenes*.

Contrary to this, death in mice pre-treated by the sub-cutaneous route either by a calcium phosphate gel, or by an aluminum hydroxide gel, in the absence of bacteria, was only delayed after injection with *Listeria monocytogenes*, with respect to the death of control mice infected in the same manner.

The protective power of CBAp40 and CBA-I fractions against infection with *Listeria monocytogenes* has been measured in the mouse. The activity of CBAp40 and CBA-LS was determined in the course of experiments whose results are assembled in Table 8 below:

TABLE 8

Protective effect against infection of mice by Listeria monocytogenes
(a) of pretreatment of the mouse by intravenous route either by CBAp40, or by CBA-LS
(b) of pretreatment of the mouse by the subcutaneous route either by CBAp40, or by CBA-LS adsorbed either on calcium phosphate (CP) or on aluminum hydroxide (AH)

| Products | Route | Death supervening at day | | | | | | | Ratio of deaths |
|---|---|---|---|---|---|---|---|---|---|
| | | 1 | 4 | 5 | 6 | 7 | 9 | 10 | |
| (CBAp40) | i.v. | 0 | 0 | 2 | 0 | 0 | 0 | 0 | 2/10 |
| (CBAp40) (CP) | s.c. | 0 | 0 | 0 | 1 | 0 | 0 | 0 | 1/8 |
| (CBAp40) (AH) | s.c. | 0 | 0 | 0 | 0 | 0 | 0 | 0 | 0/8 |
| (CBA-LS) | i.v. | 0 | 0 | 0 | 0 | 10 | 0 | 0 | 10/10 |
| (CBA-LS) (AH) | s.c. | 0 | 1 | 0 | 0 | 0 | 0 | 0 | 1/10 |
| Physiological serum | i.v. | 0 | 10 | 0 | 0 | 0 | 0 | 0 | 10/10 |

The results which are combined in this Table 8 show that the injection of *Listeria monocytogenes* to control mice resulted in 100% mortality of the animals. The prior treatment of the mice intravenously or sub-cutaneously by CBAp40 ensured 80% protection in the animals. The anti-infectious activity of CBAp40 adsorbed on a calcium phosphate or aluminum hydroxide gel enabled 90-100% protection of the animals against infection by *Listeria monocytogenes*.

Injection intravenously by CBA-LS did not exert any protective effect against infection by *Listeria monocytogenes*. On the other hand, the injection of CBA-LS adsorbed on calcium phosphate or aluminum hydroxide gel sub-cutaneously, ensured effective protection against infection by *Listeria monocytogenes*.

The results of the experiments summarized in Table 6, 7 and 8 above show clearly that both whole cells and fractions of *Corynebacterium catarrhalis* are capable of increasing significantly the resistance of the host to infection by *Listeria monocytogenes*, whether they are injected intravenously alone or sub-cutaneously as an adsorbed product either on calcium phosphate or on aluminum hydroxide in gel form.

The protection was obtained with bacteria and fractions of *Corynebacterium catarrhalis* administered intravenously, except as regards CBA-LS which does not ensure any protection by this route.

The protection is also established to be effective when the products adsorbed on calcium phosphate or aluminum hydroxide, including CBA-LS, were administered sub-cutaneously. In addition, it was verified that the injection of a gel either of calcium phosphate, or of aluminum hydroxide in the absence of the active products subjected to experimentation, did not protect mice against infection by *Listeria monocytogenes*.

It would seem that the mechanism which increases resistance to *Listeria monocytogenes* and which is conferred on the mice both by the whole cells and by the delipidized cells of *Corynebacterium catarrhalis*, and also by CBAp40 and by CBA-LS, is not the same as that by which *Corynebacterium parvum* acts, which is an aneaerobic Corynebacterium, to increase the resistance of the mice to *Listeria monocytogenes*; in fact, the increase in the resistance to *Listeria monocytogenes* ensured by *Corynebacterium parvum* is attributed to activation of fixed and free macrophages. However, this explanation does not appear to be correct for whole cells and fractions of *Corynebacterium catarrhalis*, since the latter do not increase the activity of the reticulo-endothelial system, as is the case for *Corynebacterium parvum*.

In any event, and whatever the mechanism of action, medicaments are obtained which increase the resistance to infection of individuals having an immunitary deficiency, whether it relates to patients having certain malignant tumors which increase their liability to infection by bacteria and fungi, or whether it relates to patients to whom immunosuppressor treatments have been administered such as intensive chemotherapy or radiotherapy.

What is claimed:

1. Substantially pure washed whole cells of the species *Corynebacterium catarrhalis* I-116, said cells being substantially non-toxic and having an immunostimulating effect upon administrations to test animals.

2. Delipidized whole cells having immunostimulating properties obtained by delipidizing the cells in accordance with claim 1.

3. An insoluble particulate fraction having immunostimulating properties extracted from the delipidized whole cells in accordance with claim 2.

4. A water-soluble fraction having immunostimulating properties extracted from the delipidized whole cells in accordance with claim 2.

5. An immunostimulating composition comprising an immunostimulating amount of the whole cells in accordance with claim 1 and a pharmaceutically acceptable excipient.

6. A composition in accordance with claim 5 wherein said excipient is one which makes the composition suitable for intravenous administration.

7. A composition in accordance with claim 5 wherein said excipient is an inorganic gel suitable to permit subcutaneous administration of the composition.

8. A composition in accordance with claim 5 wherein said inorganic gel is selected from the group consisting of calcium phosphate gels and alumina hydroxide gels.

9. A method for increasing the resistance to infection of animals having an immunitary deficiency, comprising administering an immunostimulating amount of the whole cells in accordance with claim 1.

* * * * *